(12) United States Patent
Sewall et al.

(10) Patent No.: US 9,555,269 B2
(45) Date of Patent: *Jan. 31, 2017

(54) CARRAGEENAN PRODUCTS AND METHOD FOR THEIR PRODUCTION AND USE

(75) Inventors: Christopher J. Sewall, Hope, ME (US); Vinayak B. Randive, Thane (IN); Vijay K. Gadkari, Mumbai (IN)

(73) Assignee: FMC Corporation, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/388,593

(22) PCT Filed: Aug. 6, 2010

(86) PCT No.: PCT/US2010/044745
§ 371 (c)(1),
(2), (4) Date: Apr. 9, 2012

(87) PCT Pub. No.: WO2011/017636
PCT Pub. Date: Feb. 10, 2011

(65) Prior Publication Data
US 2012/0189559 A1   Jul. 26, 2012

(30) Foreign Application Priority Data

Aug. 7, 2009   (IN) ............................ 1643/DEL/2009
Aug. 7, 2009   (IN) ............................ 1644/DEL/2009

(51) Int. Cl.
| | |
|---|---|
| *A61K 8/73* | (2006.01) |
| *A61K 8/72* | (2006.01) |
| *A61Q 11/00* | (2006.01) |
| *A61K 8/19* | (2006.01) |
| *A61K 8/46* | (2006.01) |
| *A61K 8/86* | (2006.01) |

(52) U.S. Cl.
CPC ............... *A61Q 11/00* (2013.01); *A61K 8/19* (2013.01); *A61K 8/463* (2013.01); *A61K 8/73* (2013.01); *A61K 8/86* (2013.01)

(58) Field of Classification Search
USPC ......................... 424/49, 401, 52, 58, 195.17
See application file for complete search history.

(56) References Cited

U.S. PATENT DOCUMENTS

| | | | |
|---|---|---|---|
| 4,702,905 A * | 10/1987 | Mitchell et al. | 424/57 |
| 6,387,354 B1 | 5/2002 | Bixler et al. | |
| 7,189,843 B2 * | 3/2007 | Tsai et al. | 536/114 |
| 2002/0110539 A1 | 8/2002 | Zhu et al. | |
| 2004/0062681 A1 | 4/2004 | Winston | |
| 2008/0033392 A1 | 2/2008 | Gaserod et al. | |
| 2008/0152585 A1 | 6/2008 | Ryde et al. | |

FOREIGN PATENT DOCUMENTS

| | | |
|---|---|---|
| JP | 10025302 | 1/1998 |
| WO | WO 99/44571 | 9/1999 |

OTHER PUBLICATIONS

Notification of Transmittal of The International Search Report and The Written Opinion of The International Searching Authority, or the Declaration, International Application No. PCT/US2010/044745, International Filing Date—Aug. 6, 2010.

* cited by examiner

Primary Examiner — Lezah Roberts
(74) Attorney, Agent, or Firm — FMC Corporation

(57) ABSTRACT

The present invention is directed to a carrageenan product comprising a semi-refined, alkali treated iota carrageenan wherein the semi-refined, alkali treated iota carrageenan has: (i) a viscosity of 18 cP to 83 cP, (ii) a particle size of at least 90% passing through a #100 US sieve mesh and at least 20% passing through a #230 US sieve mesh, and (iii) a fraction of sodium cations of at least 35%, wherein the fraction of sodium cations is determined by the weight of sodium cations divided by the sum of the weight of sodium cations and potassium cations. This invention is also directed to toothpaste compositions comprising the carrageenan product of the invention.

29 Claims, No Drawings

CARRAGEENAN PRODUCTS AND METHOD FOR THEIR PRODUCTION AND USE

FIELD OF THE INVENTION

The present invention is directed to carrageenan products; semi-refined, alkali treated iota carrageenans; and toothpaste formulations containing such carrageenan products and semi-refined, alkali treated iota carrageenans.

BACKGROUND OF THE INVENTION

Carrageenan is a complex mixture of sulfated polysaccharides comprising linear polymers of 1→3 linked [α]-D-galactose units and 1→4 linked [β]-D-galactose units. Carrageenan is produced by red seaweeds where it functions as the principle structural polysaccharide. It is located within the cell wall and intra-cellular matrix of the plant tissue. The carrageenan content of commercially harvested seaweeds is generally between 30% and 80% based on the seaweed dry weight.

Carrageenan finds wide applicability as a food ingredient and is functional in foods such as dairy products, water dessert gels, meat products, confections, beverages, dressings and other such products. Carrageenan is also useful in products such as cosmetics, toothpaste and other personal care products, in soft gel capsules, and in other industrial, medical, pharmaceutical, and agricultural applications.

The molecular weight of carrageenan products is typically from about 100,000 to about 1,000,000 Daltons. Carrageenans have the ability to form an almost infinite variety of gels at room temperature with a variety of gelling and melting points. Carrageenan solutions can thicken, suspend, and stabilize particulates, colloidal dispersions and water/oil emulsions. The solutions shear thin, which allows them to be pumped easily. Also, the sheared solutions rapidly rebuild viscosity and suspending power upon standing. Depending upon the application, carrageenans present in parts per million up to a few percent by weight provide gelling, thickening, suspending, binding and/or generate a desired product feel or texture.

Carrageenan is generally soluble in warm water, in which it forms a viscous solution. It is insoluble in most organic solvents and typically forms complexes with proteins. The major types of carrageenan are designated as Kappa, Iota, Lambda, Nu and Mu. These are differentiated based on the nature of the repeating galactose units contained in the carrageenan. The polymer chain can be cleaved by hydrolytic depolymerization upon treatment with an acid or by oxidative depolymerization upon treatment with hydrogen peroxide.

In a typical process for producing refined carrageenan, crude seaweed is first washed with cold water or seawater to remove sand and other particles that may be present after seaweed has been harvested. Carrageenan typically does not swell during the cold wash, primarily because carrageenan in seaweed is associated with structural components of the seaweed, generally cellulose. Depending upon the seaweed species, following the cold wash, a hot water extraction process is typically performed in which the extracted carrageenan is treated with an aqueous base at high temperature. Generally, the base used is an alkali or alkaline earth metal hydroxide such as, for example, sodium hydroxide, calcium hydroxide, or potassium hydroxide. This high temperature aqueous base modification step leads to the formation of 3,6-anhydro linkages in the galactose units of the carrageenan. After this modification, the hot extract is filtered to remove insoluble materials such as cellulose, hemicelluloses and other particulates and acid is added to adjust the pH to 7.5 to 10.5. The filtrate can then be concentrated to about 4% carrageenan for further processing. Optional process steps after extraction include centrifugation and bleaching. Refined carrageenan is typically obtained by precipitation of the extract from the aqueous solution with potassium chloride or an alcohol such as isopropyl alcohol. The resulting carrageenan product is subsequently dried and ground.

Material throughput for production of refined carrageenan on a commercial scale is rate limited. After the extraction step, a hot aqueous stream can typically only contain low concentrations of carrageenan, typically up to about 4%. At higher concentrations of carrageenan, the aqueous stream becomes too viscous to process efficiently.

There has been an ongoing search for more cost-effective methods of preparing semi-refined carrageenan and other carrageenan products as lower cost replacements for conventional refined carrageenan. Semi-refined carrageenan (SRC) products are those in which few or none of the structural components of the seaweed, principally cellulose, have been removed. During production of SRC, a salt such as potassium chloride or sodium chloride is added during the base modification along with the base. The presence of sufficient amounts of salt prevents disintegration of the seaweed structure and inhibits extraction of carrageenan from the seaweed. An alcohol such as isopropyl alcohol can also be used alone or in combination with salt to inhibit extraction of the carrageenan. Following the base modification step, with the seaweed structure still intact, the processed seaweed is typically dried to afford SRC. When the seaweed is a member of the *Euchema* family, the SRC obtained is known as processed *Euchema* seaweed (PES).

U.S. Pat. No. 5,801,240 to Rideout et al. discloses a method for producing semi-refined kappa carrageenan. It describes the conventional PES production process with improvements including better monitoring of oxidation-reduction potential of the potassium hydroxide (KOH) solution used in the extraction method and optionally chopping the seaweed prior to KOH cooking. U.S. Pat. No. 5,777,102 to Larsen discloses a modified carrageenan made by partially hydrating seaweed in water/solvent/base mixture to get modification of the carrageenan following which the material is extruded. U.S. Pat. No. 5,502,179 to Larsen discloses a method in which seaweed is reacted under heating in a solvent/water/base mixture to get fully modified carrageenan followed by extrusion to obtain a product with a specific light transmission and Brabender profile. WO 03/059956 to Therkelsen discloses a heterogeneous carrageenan manufacturing process from mono-component seaweed with reduced use level of KOH. This is an improved cost effective method of making carrageenan extract or PES that uses high salt level in combination with NaOH to reduce the level of costly KOH. U.S. Pat. No. 6,479,649 B1, U.S. Pat. No. 7,018,635 B2, and U.S. Pat. No. 7,189,843 B2 to Tsai et al. disclose a method for production of carrageenan and carrageenan products with its main focus on extrusion of seaweed feedstock. U.S. Pat. No. 6,387,354 B1 to Bixler et al. discloses a binder for a toothpaste composition comprising semi-refined kappa and/or semi-refined iota carrageenans in combination with other binder components. Japanese Patent Publication No. JP8005921B2 discloses a modified iota carrageenan having a viscosity of 5 cP to 40 cP in a 1.5% aqueous solution at 75° C. In this disclosure, a part of iota carrageenan can be replaced by lambda carrageenan for a ratio of iota to lambda carrageenan that is 1 to 4 or higher.

A mixture of these carrageenans in such a ratio when used as a binder exhibits an effect of stabilizing the quality of toothpaste nearly the same as obtained when iota carrageenan is used alone. Japanese Patent Publication No JP2752610B2 discloses a modified iota carrageenan with a viscosity of 5 cP to 40 cP at 75° C. obtained from *Euchema spinosum* by hydrolyzing its extract with alkali hydrolysis, acid hydrolysis, hydrolysis using an oxidant, or hydrolysis with an enzyme or other microorganisms. When used as a stabilizer in toothpaste formulations, this modified iota carrageenan is preferably compounded with materials like calcium phosphate, glycerol, etc. Japanese Patent Publication No. JP2752611B2 discloses toothpaste comprising lambda carrageenan and modified carrageenan the aqueous 1.5% solution of which has a viscosity of 5 cP to 40 cP at 75° C.

Refined carrageenans have some advantages to SRC obtained from the same seaweeds. Refined carrageenans typically hydrate, i.e. begin to swell and become soluble, at lower temperatures than SRC. Another advantage of refined carrageenans is that because SRC contains cellulosics and other materials which are absent in refined carrageenans, gels formed from SRC have a lower clarity compared to gels prepared from refined carrageenan products. There remains a continued need for development of improved low cost, quality SRC products for use in marketable formulations for industrial and consumer applications such as toothpastes.

SUMMARY OF THE INVENTION

The present invention is directed to a carrageenan product comprising a semi-refined, alkali treated iota carrageenan wherein the semi-refined, alkali treated iota carrageenan has: (i) a viscosity of 18 cP to 83 cP, (ii) a particle size of at least 90% passing through a #100 US sieve mesh and at least 20% passing through a #230 US sieve mesh, and (iii) a fraction of sodium cations of at least 35%, wherein the fraction of sodium cations is determined by the weight of sodium cations divided by the sum of the weight of sodium cations and potassium cations. This invention is also directed to toothpaste compositions comprising the carrageenan product of the invention.

DETAILED DESCRIPTION OF THE INVENTION

Carrageenans are large flexible molecules which curl forming helical structures. This gives them the ability to form a variety of gels at room temperatures. They are widely used in food, personal care or industrial applications as a thickening and stabilizing agent. A particular advantage is that they provide thixotropy, i.e, the ability to thin and flow under shear stress and recover their viscosity once the stress is removed. There are three main commercial classes of carrageenans: Kappa carrageenans, produced from *Kappaphycus alvarezii*, also called *Euchema cottonii*, form strong rigid gels. Iota carrageenans, produced from *Euchema denticultum*, also called *Eucheuma spinosum*, form flexible soft gels. Lambda carrageenans form gels when mixed with protein rather than water and are used for thickening dairy products. The most common source of lambda carrageenan is *Gigantina* from South America. Depending upon the application, carrageenans present in parts per million up to a few percent by weight provide gelling, thickening, texturizing, suspending, and/or binding properties. Moreover, carrageenan can generate desirable product feel. Consequently, carrageenan finds wide applicability as a food ingredient and is functional in foods such as dairy products, water dessert gels, meat products, confections, beverages, dressings and other such products. Carrageenan is also used in products such as cosmetics, toothpaste, and other personal care products, and in industrial, medical, and agricultural applications.

The present invention relates to a carrageenan product containing iota carrageenan, particularly, a semi-refined, alkali treated iota carrageenan from *Euchema* seaweed in which all or part of the cellulosics are retained. The modification process according to the method of the present invention and post modification treatment steps help to make the semi-refined, alkali treated iota carrageenan of the present invention an ideal thickening agent in toothpaste formulations. Other commercial SRC presently available have poor heat shock properties that result in an increase in viscosity (thickening) of the toothpaste to an unacceptable level. In contrast, the semi-refined, alkali treated iota carrageenan of the present invention exhibits low heat shock properties that are acceptable in toothpaste.

The present invention is also directed to the semi-refined, alkali treated iota carrageenan having: (i) a viscosity of 18 cP to 83 cP, (ii) a particle size of at least 90% passing through a #100 US sieve mesh and at least 20% passing through a #230 US sieve mesh, and (iii) a fraction of sodium cations of at least 35%, wherein the fraction of sodium cations is determined by the weight of sodium cations divided by the sum of the weight of sodium cations and potassium cations. The carrageenan product of the present invention can be solely comprised of such semi-refined, alkali treated iota carrageenan.

An alkali treated iota carrageenan product, as used herein, means using an alkali to process the seaweed, which results in an iota carrageenan with a level of 3,6 anhydro galactose that is higher than in its native or natural form. The alkaline treatment converts nu carrageenan (which is present in the seaweed) to iota carrageenan, which is also present in the seaweed. The resulting iota carrageenan comprises about 76 to 100 mol % iota carrageenan. In its native or natural form, iota carrageenan is generally in the range of from 70-75 mol % iota carrageenan. As used herein, the alkali processed seaweed contains iota carrageenan in the range of 76-100 mol % iota.

The semi-refined, alkali treated iota carrageenan of the invention may be prepared in a manner illustrated by the examples. Generally, the methods comprise wet treatment steps to produce the semi-refined, alkali treated iota carrageenan of the invention followed by drying and grinding. Wet treatment steps include washing the seaweed, treating the seaweed with a base, such as sodium hydroxide, at a temperature from about 25° C. to about 65° C., and rinsing the treated seaweed. Wet treatment steps employ processing liquids with sufficient salt or alcohol to minimize the solubilization and loss of carrageenan during processing. Alcohol washing or ion exchange steps may be employed with compositions and concentrations needed to achieve the desired cation balance of the semi-refined, alkali treated iota carrageenan including use of recycle streams for cost effective operation. The dried powder is further processed to reduce particle size in one or more grinding steps. The seaweeds used in the examples are iota carrageenan-containing seaweeds, namely, *E. denticulatum* (commonly referred to as *Euchema spinosum*).

"Separate" as used herein means to move substantially apart. In particular, a solid, such as seaweed, is separated from a liquid, or vice versa, by means that can include draining, wringing, centrifuging, squeezing, and the like. By "substantially" in the context of separation of solid and liquid is meant that the resultant solid can be dry, moist, or wet, but not suspended in liquid. "Washing" means suspending a solid, e.g. seaweed, in a liquid or running a stream of liquid over one or more surfaces of a solid with the intent of removing liquid-soluble constituents.

During production, salts such as potassium chloride (KCl) or sodium chloride (NaCl) can be used during modification and treatment steps to prevent breakdown of the seaweed structure and inhibit release of carrageenan from seaweed. Alternatively, an alcohol, such as isopropyl alcohol, can also be used to inhibit release of carrageenan from the seaweed structure. Following a base modification step, with the seaweed still intact, the processed seaweed mixture is typically washed and dried to afford the semi-refined, alkali treated iota carrageenan of the invention.

The viscosity of the semi-refined, alkali treated iota carrageenan of the present invention is 18 cP to 83 cP, more particularly, 20 cP to 40 cP and 20 cP to 30 cP. Viscosity can be controlled by processing conditions such as the time and temperature of the base modification step. A bleach step is useful to improve color and to produce reduced viscosity materials useful in formulations like toothpaste. To obtain higher viscosity materials, the level of bleach may be reduced or the bleaching step may be omitted.

This particle size of the semi-refined, alkali treated iota carrageenan of the invention is as follows: at least at least 90% passes through a #100 US sieve mesh (149 micron) and at least 20% passes through a #230 US sieve mesh (63 micron). A preferred particle size of the semi-refined, alkali treated iota carrageenan of the invention is as follows: at least at least 90% passes through a #100 US sieve mesh (149 micron), at least 60% passes through a #230 US sieve mesh (63 micron), and at least 60% passes through a #325 US sieve mesh (44 microns). In another embodiment of the invention 100% of the semi-refined, alkali treated iota carrageenan passes through a #100 US sieve mesh. The preferred particle size of the semi-refined, alkali treated iota carrageenan of the present invention can be achieved in the grinding step. The preferred particle size can be achieve in the grinding step by conventional particle size reduction techniques such as grinding and sieving, impact milling, jet milling, disaggregation and particle impingement.

It is desired to maintain a cation balance such that the fraction of sodium cations in the semi-refined, alkali treated iota carrageenan is at least 35% by weight wherein the fraction of sodium cations is determined by the weight of sodium cations divided by the sum of the weight of sodium cations and potassium cations. Sodium cation content in the semi-refined, alkali treated iota carrageenan of the invention may also be at least 50%, at least 75%, at least 90%, based on the weight of the sodium and potassium cations. The potassium content of the semi-refined, alkali treated iota carrageenan is preferably less than 4.5% by weight. The cation balance can be controlled by means known in the art including selection of processing ingredients, washing, and the like.

The semi-refined, alkali treated iota carrageenan of the present invention can be prepared from *Euchema spinosum* seaweed by a process comprising: (a) optionally washing raw seaweed with an aqueous NaCl solution, such as about a 1.5 wt % solution of NaCl; (b) modifying the seaweed by treating with an aqueous NaOH and NaCl solution at a temperature of at least about 40° C.; (c) washing the seaweed at neutral pH at least once or at least twice; (d) chopping the seaweed to a size that passes through a one inch screen; (e) optionally bleaching the seaweed and then washing with water; (f) drying the seaweed to a moisture content of less than 15% (w/w) moisture content; and (g) grinding the seaweed to the required particle size; wherein the seaweed may be extruded after any of steps (e), (f) or (g) or may not be extruded at all; and wherein steps (d) and/or (e) can precede step (b). Step (e) can precede step (d). The NaOH concentration in the modification step can be about 1% to about 10% by weight of the aqueous solution, preferably, about 1.5% to about 6% by weight, more preferably, about 2% to about 5% by weight, yet more preferably about 3% to about 4% by weight. More specifically, the NaOH concentration can be about 3.6% by weight. The NaCl concentration in the aqueous solution of the modification step can be about 2% to about 50% by weight of the aqueous solution, preferably about 5% to about 30%, more preferably, about 12% to about 20%, and yet more preferably about 14% to about 18%. More specifically, the NaCl concentration can be about 16%. The temperature in the modification step can be about 30° C. to about 60° C., more preferably, about 40° C. to about 50° C. More specifically, the temperature is about 40° C. In another embodiment, the temperature is about 45° C. When bleaching the seaweed, NaOCl can be used. Suitable concentrations of NaOCl include about 0.18 wt % to about 0.9% wt %. A preferred range is about 0.18 wt % to about 0.72 wt %. Typically, about 0.36 wt % NaOCl can be used. Grinding can be accomplished by any means known in the art. The semi-refined, alkali treated iota carrageenan may, optionally, be alcohol washed prior to or after grinding.

The semi-refined, alkali treated iota carrageenan may be further processed after grinding and/or washing after grinding, by ion exchange. A chelator, e.g. EDTA, is preferably used to enhance ion exchange. The EDTA can be $Na_4$EDTA. A range of concentrations of EDTA are suitable, including about 0.1% to about 2% wt/vol, preferably, 0.2% to about 1%, more preferably about 0.4 to about 0.6%. In one embodiment, the EDTA concentration is about 0.5%. The ion exchange can be carried out in aqueous alcohol. The alcohol concentration can be about 40% to about 90% (vol/vol), preferably about 50% to about 80%, more preferably about 60%.

After ion exchange, the semi-refined, alkali treated iota carrageenan can be further processed by alcohol washing using aqueous alcohol. The alcohol concentration can be about 40% to about 90% (vol/vol), preferably about 50% to about 80%. More preferably, a graduated series of washes having increasing alcohol concentration are used, from about 50%, about 60%, about 70%, about 80%, and even about 90%. Some or all alcohol concentrations may optionally be omitted or repeated. Any hydrophilic alcohol can be used for alcohol washing. Preferred alcohols include ethanol, n-propanol, and, particularly, isopropanol.

The ingredients of the toothpaste of the present invention may be broadly divided into active ingredients and inactive ingredients as listed below. Active ingredients provide at least one chemical or biological functionality.

Active ingredients include fluoride; antibacterial agents such as triclosan to control plaque; desensitizing agents; anti-tartar agents; sodium bicarbonate (baking soda); enzymes, to enhance the antibacterial properties of saliva; non-sugar sweetener, such as xylitil, which reduces levels of cariogenic (decay causing) bacteria in the mouth; herbal extracts; whitening agents, such as peroxides; functional inclusions or encapsulated functional agents and bioadhesive additives.

Other ingredients include abrasives; foaming agents; thickeners (also called binders or binding agents); humectants; flavoring, sweetening, and coloring agents; preservatives; decorative pigments or inclusions; and water.

The basic ingredients for most toothpaste are abrasives, foaming agents, binders, humectants and water. Fluoride can also be used in toothpaste. Additional ingredients are sweeteners, flavoring agents, coloring agents and preservatives.

Fluoride incorporates itself into tooth enamel making the teeth more resistant to acids produced by plaque bacteria, as well as acids found in fruit juices, soda drinks (both regular and diet), and certain foods. In toothpaste, fluoride is in the form of sodium monofluorophosphate, stannous fluoride, or sodium fluoride.

Abrasives give toothpaste its cleaning power. They remove stains and plaque, as well as polish teeth. Common abrasives include calcium phosphates, alumina, calcium carbonate (chalk) which may be precipitated or natural, and silica. Cellulose particles such as microcrystalline cellulose provide a mild abrasive effect. Toothpaste should be abrasive enough to remove plaque and stains, but not abrasive enough to damage tooth enamel.

Foaming agents create the foaming action commonly associated with toothpastes. Foam assists in removal and suspension of displaced biofilm and food particulates during toothbrushing. Sodium lauryl sulfate (SLS) is a preferred foaming agent.

Humectants give toothpaste its texture and retains moisture so that the toothpaste does not dry out. Glycerin and sorbitol are common humectants. Xylitol is an uncommon, but superior humectant, which also boosts fluoride's cavity fighting power. Water is also a humectant, but is accounted separately.

Binders thicken toothpastes to prevent separation of the solid and liquid components, especially during storage. They also affect the speed and volume of foam production, the rate of flavor release and product dispersal, the appearance of the toothpaste ribbon on the toothbrush, and the rinsibility from the toothbrush. Binders also help to create the texture of toothpaste and determine the viscosity of the toothpaste.

The toothpaste of the present invention comprises the carrageenan product containing the semi-refined, alkali treated iota carrageenan of the present invention as a binder. As mentioned above, the carrageenan product may solely be comprised of the semi-refined, alkali treated iota carrageenan of the invention. Other binders may be included such as refined carrageenans, other semi-refined carrageenans, xanthan, carboxymethyl cellulose (CMC), and carbopol. Other thickeners that may be included are bentonite, magnesium aluminum silicate, colloidal grades of microcrystalline cellulose and silica, and sodium alginate. The total amount of all binders may be 0.3 wt. % to 2.0 wt. % of the toothpaste formulations. The semi-refined, alkali treated iota carrageenan of the present invention may be present in an amount up to 10% of the total binder by weight; up to 20% of the total binder; between 20% and 50% of the binder; more than 31% of the binder; between 35% to 75% of the binder; more than 50% of the binder; or between 50% to 100% of the binder.

Preservatives prevent the growth of microorganisms in toothpaste which eliminates the need to refrigerate toothpaste. Common preservatives include sodium benzoate, methyl paraben, and ethyl paraben. Flavoring agents such as peppermint, spearmint, cinnamon, wintergreen, and menthol are added to improve the taste of toothpaste and to cover up the taste of most foaming agents, especially SLS. In addition, flavors help create fresh breath and a clean feeling sensation. Sweeteners also improve the taste of toothpaste. Most toothpaste sweeteners are artificial and contribute very little to cavity formation. Saccharin is a common toothpaste sweetener. Coloring agents provide toothpaste with pleasing colors. Artificial dyes and pigments are used to make red, green, and blue toothpastes. Titanium dioxide is used to make some toothpaste white.

To further improve shelf life of the toothpastes of the present invention, one may include polyethylene glycol. A typical amount for such purpose would be from 1 to 5 wt % of polyethylene glycol, more particularly, 2 wt %. Typical polyethylene glycols include those having an average molecular weight of between 150 to 650 such as those having an average molecular weight of between 190 to 210 (e.g., PEG 200); an average molecular weight of between 285 to 315 (e.g., PEG 300); an average molecular weight of between 380 to 420 (e.g., PEG 400); and an average molecular weight of between 570 to 630 (e.g., PEG 600).

After the abrasive, the water, the binder and other ingredients have been accounted for, the humectants account for the balance of material. Typically, as the amount of water is increased, the amount of other humectants in the toothpaste composition decreases. The toothpaste composition typically comprises 8 to 50 weight % of humectants on an absolute basis, i.e. exclusive of any water that is present in the humectants. Sorbitol used as a humectant is, for example, available as 70% sorbitol and 30% water.

The toothpaste composition typically comprises about 0.8 wt % to about 3 wt. %, preferably about 1% to 2.5 wt. %, of a surface-active foaming agent like SLS. A flavoring agent when present typically comprises about 0.1% to about 2 wt. %, more typically, about 0.5% to about 1.5 wt %. When a sweetener is present, the toothpaste composition typically comprises about 0.1% to about 2 wt. % of the sweetener.

The semi-refined, alkali treated iota carrageenan of the invention can partially or fully substitute for other conventional binders used in toothpaste in addition to reducing cost by substituting for binders such as refined iota carrageenans at the same use level (0.3 wt. % to 2.0 wt. %).

Toothpaste compositions can be prepared using either the hot process or the ambient process, and either a batch process or a continuous process may be used. The ambient process is sometimes called the cold process. The hot process is described, for example, in Scott, U.S. Pat. No. 4,353,890, and Ballard, U.S. Pat. No. 6,187,293, the disclosures of which are incorporated herein by reference. A continuous process for the manufacture of toothpaste is disclosed, for example, in Ballard, U.S. Pat. No. 6,187,293, the disclosure of which is incorporated herein by reference. A continuous process for the manufacture of toothpaste is also disclosed in Catiis, U.S. Pat. No. 5,236,696.

The disclosure of all references cited herein is incorporated herein by reference, in their entireties.

The following procedures were used to characterize the semi-refined, alkali treated iota carrageenan of the invention.

The viscosity is measured using a Brookfield RTV with appropriate speeds and spindles and reported in centipoises (cP). Samples for viscosity testing are prepared by dispersing 7.5 grams of carrageenan powder in 450 grams of deionized water, adding further deionized water to reach 500 grams (net weight), stirring while heating to 85° C., holding for 15 minutes at 85° C., adding back deionized water (as needed) for 1.5% solids, cooling with continuous stirring and testing viscosity when equilibrated at 75° C. The acid insoluble matter (AIM) content of the carrageenan is the percent of dry residue recovered by filtration after treatment of a 2 gram sample of the carrageenan powder with 150 grams of deionized water and 15 ml of 10% sulfuric acid at 100° C. for 6 hours. The gel strength properties of water gels containing 2% carrageenan powder (with or without added salt) were tested using an Instron at 25° C. with a 21.5 mm diameter tapered plunger and at a rate of 70 mm/minute. The break force (in grams) and penetration distance (in centimeters) of the plunger into the gel is recorded as the average for three gels. The 2% water gels (WG) were prepared by dispersing 10 grams of carrageenan powder in 450 ml of deionized water, adjusting to 500 grams net weight with deionized water, heating to 85° C., holding at temperature for 15 minutes, replacing water lost by evaporation, dividing the sample into 3 dishes, and placing them into a cooling bath for one hour at 10° C. before inverting the gel onto a petri for testing. Modified water gels (Mod WG) were prepared in a similar manner but adding 1 gram of potassium chloride and 1 gram calcium chloride dehydrate with the 10 gram carrageenan sample. Milk gels were prepared by dispersing 1 gram of carrageenan powder into 486 grams of cold homogenized milk (3 to 4% butterfat), agitating while heating the sample to 82° C. in a boiling water bath, adjusting for water lost by evaporation, then dividing the sample between three dishes and placing in a 10° C. bath for an hour prior to testing.

Particle size by sieve mesh analysis was determined by adding 50 grams of carrageenan powder sample to the top sieve of a stack of sieves arranged in decreasing mesh size with the coarsest sieve on top and a closed pan on the bottom. The stainless steel sieves are compliant with ASTM standard E-11 specifications with a nominal sieve opening in microns: #80 US sieve mesh (180 microns), #100 US sieve mesh (149 microns), #120 US sieve mesh (125 microns), #140 US sieve mesh (106 microns), #170 US sieve mesh (90 microns), #200 US sieve mesh (75 microns), #230 US sieve mesh (63 microns), #270 US sieve mesh (53 microns), #325 US sieve mesh (44 microns), #400 US sieve mesh (38 micron). The covered sieve stack is placed in a Ro-Tap Model RX-29 sieve shaker and the timer is set for 15 minutes. The weight of sample remaining on each sieve is determined and the percentage of powder passing through each sieve is calculated.

The utility of a carrageenan binder in a toothpaste formulation is determined by measuring the strength, stability and texture of a toothpaste formulation. A traditional method of measuring toothpaste strength, stability and texture uses the Cuban rating system wherein the toothpaste is squeezed over a Cuban rack. The ability of the strands to remain suspended over the bar with numbered size increments of 1 to 12 determines the rating 1 to 12 given to the toothpaste. The stainless steel rods are spaced at increasing distances apart starting at 3 mm between rods 1 and 2 (space number 1) with the distance between rods increases by 3 mm from rod to rod. Thus, the distance between rods 2 and 3 is 6 mm, and the distance between the twelfth and thirteenth rod (space number 12) is 39 mm. In the Cuban test, a sample is smoothly extruded from toothpaste tube with a nozzle attached held at a angle of 45 degrees such that a ribbon of paste is deposited across the rack in about 2 to 4 seconds. The toothpaste ribbon is allowed to stand for 30 seconds then the point at which the ribbon breaks is recorded as the Cuban reading. The test is performed five times. The Cuban rating is the average of the five readings rounded to the nearest figure Measurements are typically made over a period of time (such as initial, 1 day, 3 weeks, 6 weeks storage) to determine the strength, texture, and stability upon storage. Heat shock is an undesirable change (increase or decrease) of more than 3 Cubans after storage at 50° C.

The present invention is now described in more detail by reference to the following examples, but it should be understood that the invention is not construed as being limited thereto. Unless otherwise indicated herein, all parts, percents, ratios and the like are by weight.

EXAMPLES

The following procedure was used to prepare toothpaste batches under the hot process. The specific toothpaste formulations that were tested below were a chalk based toothpaste wherein the binder comprised 36% conventional extract iota carrageenan and 50% semi-refined, alkali treated iota carrageenan of the present invention (the balance being 14% silica). The conventional extract iota carrageenan that was used in the testing below was the same and had a viscosity of about 24 cps. The amount of the conventional carrageenan replaced with the lower cost semi-refined, alkali treated iota carrageenan of the invention is considered to be a relatively large amount and a significant indicator of the functionality of the semi-refined, alkali treated iota carrageenan of the invention in toothpaste. The semi-refined, alkali treated iota carrageenan samples of the present invention, as well as those outside the present invention, used in the Examples herein were made using similar processes with minor variations and the characteristics of each carrageenan are set forth in the following table. In general, the process that was used was: (a) raw seaweed was washed with an aqueous 1.5 wt % NaCl solution; (b) the seaweed was modified by treating such with an aqueous NaOH and NaCl solution at a temperature of about 45° C.; (c) the seaweed was washed twice at a pH of about 8; (d) the seaweed was then dried and ground to a size as noted in the following Table; and (e) either alcohol washed (three times with increasing amounts of isopropanol) or ion exchanged (in EDTA/NaCl alcohol) as noted in the following Table.

Carrageenan Samples

|  | Inventive CGN 1 | Inventive CGN 2 | Inventive CGN 3 | Inventive CGN 4 | Comparative CGN A | Comparative CGN B |
|---|---|---|---|---|---|---|
| Alcohol Wash | Yes | Yes | Yes | No | Yes | Yes |
| Ion Exchange | No | No | Yes | No | Yes | No |
| Ph | 9.5 | 10.7 | 9.34 | 9.1 | 9.6 | 9.6 |
| 100 mesh | 99 | 98 | 99 | 97 | 99 | 96 |
| 230 Mesh | 27.8 | 35 | 20.3 | 33 | 32 | 37 |
| Viscosity | 46 | 83 | 52 | 18 | 185 | 13 |
| K | 0.0 | 0.4 | 0.0 | 0.60 | 0.5 | 0.50 |
| Na | 6.9 | 8.3 | 11.1 | 8.11 | 6.7 | 5.37 |
| Na Fraction | 100% | 95% | 100% | 93% | 93% | 91% |

The blend ratio in the binders was as follows:
Inventive Carrageenan Binder Blends

| Blends Composition Products | Inventive Blend 1 % w/w | Inventive Blend 2 % w/w | Inventive Blend 3 % w/w | Inventive Blend 4 % w/w |
|---|---|---|---|---|
| Iota Carrageenan | 36 | 36 | 36 | 36 |
| CGN 1 | 50 | — | — | — |
| CGN 2 | — | 50 | — | — |
| CGN 3 | — | — | 50 | — |
| CGN 4 | — | — | — | 50 |
| Silica | 14 | 14 | 14 | 14 |

Comparative Carrageenan Binder Blends

| Blends Composition Products | Comparative Blend 1 % w/w | Comparative Blend 2 % w/w |
|---|---|---|
| Iota Carrageenan | 36 | 36 |
| CGN A | 50 | — |
| CGN B | — | 50 |
| Silica | 14 | 14 |

The details of the tested toothpastes are as follows:

| Ingredients | Amount in Grams |
|---|---|
| Carrageenan Binder Blend | 8.00 |
| Glycerin | 100.00 |
| Sorbitol | 170.00 |
| Saccharin | 2.0 |
| Sod Benzoate | 3.0 |
| Chalk | 460.0 |
| Flavor | 10.0 |
| SLS | 20.0 |
| Water | 227.0 |
| Total | 1000.0 |

Procedure Used for Making the Toothpaste Tested Herein 8 grams of each Carrageenan Binder Blend was dispersed in to the pre-mixed Humectants Blend (100 grams Glycerin+ 170 grams Sorbitol) and stirred for 5 minutes. 227 grams of preheated water was added and stirring was continued at 65° C. for 10 mins. 2 grams of saccharin and 3 grams sodium benzoate were added to the elixir and stirring continued at 65° C. for 10 minutes. The above elixir was transferred to a Ross double planetary vacuum mixer equipped with a vacuum Mixer. 460 grams of chalk abrasive were added and mixed well under the vacuum for 15 minutes (Vacuum 760 mm/Hg). 10 grams of flavor was added and mixed well under the vacuum for 10 minutes. 20 grams SLS were added and mixed well under the vacuum for 20 minutes. The batch was discharged for testing and filling.

Testing Procedures

The above toothpaste samples were tested using the following two testing methods.

Toothpaste Viscosity Measurement

The toothpaste viscosity was measured using a Brookfield DV-II+ Viscometer in accordance with the following: Spindle No.: T-E; Spindle Speed: 5 RPM; Temperature: 25 Deg C.; Viscosity Unit: Torque (%) (1%=10,000 centipoises; and Method: Helipath).

The toothpaste was squeezed into a 100 ml beaker. The spindle was positioned above the surface of the toothpaste. The spindle was rotated at 5 RPM and the helipath attachment switched on to commence downward movement of the spindle. The viscosity was recorded as soon as the spindle reached 3 cm below the surface of the toothpaste.

Cuban Test

In the Cuban test (also termed the "Rack" test), the paste was squeezed from a tube through a fixed orifice across a grid of parallel rods, increasingly spaced apart. The test results are expressed as the greatest space number (numbers are from 1-12), which represents the longest distance between rods that support the dentifrice ribbon without having it break. The rack was about 300 millimeters (mm) long and about 100 mm wide. The stainless steel rods were spaced at increasing distances apart starting at 3 mm between rods 1 and 2 (space number 1) and the distance between rods increases by 3 mm from rod to rod. Thus, the distance between rods 2 and 3 was 6 mm, and the distance between the twelfth and thirteenth rod (space number 12) was 39 mm. For toothpastes that are not high moisture toothpastes when measured at room temperature, ratings of 1-2 and 9-12 were not acceptable, 3 and 8 were acceptable and 4-7 were good. For toothpastes that are not high moisture toothpastes when measured at 40° C., ratings of 1-2 and 10-12 were not acceptable, 3 and 8-9 were acceptable and 4-7 were good. To carry out the Cuban test, the following procedure was followed. A nozzle was fixed to a toothpaste tube filled with a toothpaste composition to be tested. The tube filled with test toothpaste composition and having the nozzle attached was held at an angle of 45 degree to the rack device. Pressure was applied at the bottom of the tube and a uniform ribbon of paste was squeezed from the tube. While the ribbon of paste was being extruded from the tube the tube was moved across the rack in a straight line. The time to stretch the ribbon of paste over the rack was usually about two to four seconds. If the ribbon breaks before the entire rack was traversed, the procedure was repeated. The ribbon was allowed to stand for 30 seconds. At that time, the point at which the ribbon breaks was recorded as the rack rating or Cuban value. The test was performed five times and the average reading is recorded, rounding off to the nearest complete figure.

Phase Separation in Toothpaste

One of the main forms of instability in toothpaste is known as phase separation. The main indication of phase separation is when the liquid component of toothpaste separates out from the toothpaste ribbon and comes out as oil or water when the paste is squeezed from the tube on the paper. Stability tests were conducted by filling tubes with the sample paste. The tubes were capped and stored flat at room temperature and at 40° C. The test was performed after the 3, 6, 9, 12 week exposure on the samples kept at room temperature and at 40° C. and the observations are recorded each time. A toothpaste ribbon of about 5 cm in length was squeezed from the tube and examined visually. Any occurrence of separate oily phase, water phase or oozing of liquid was considered as a stability defect.

Results

The following data demonstrate both the acceptable Cuban values, viscosities and flavor separation for the present invention.

CHALK (10-17) TOOTH PASTE
(INITIAL PROPERTIES, RT AND 40° C. STORAGE TEMPERATURE STABILITY)

| | Examples | | | |
|---|---|---|---|---|
| | Toothpaste 1 | Toothpaste 2 | Toothpaste 3 | Toothpaste 4 |
| Carrageenan Process | 1 HOT | 2 HOT | 3 HOT | 4 HOT |
| Alcohol wash | | | | With IPA Wash |
| Toothpaste Visc (1 Day) | 30.6 | 20.4 | 27.4 | 22.1 |
| Cuban (1 Day) | 7 | 4 | 7 | 4 |
| RT Stability | | | | |
| 3 Week | Good | Good | Good | Good |
| 3 Week Cuban | 7 | 4 | 6 | 3 |
| 3 Week Viscosity | 28.5 | 18.2 | 25.6 | 19.7 |

CHALK (10-17) TOOTH PASTE
(INITIAL PROPERTIES, RT AND 40° C. STORAGE TEMPERATURE STABILITY)

| | Examples | | | |
|---|---|---|---|---|
| Carrageenan Process | Toothpaste 1 HOT | Toothpaste 2 HOT | Toothpaste 3 HOT | Toothpaste 4 HOT |
| 6 Week | Good | Good | Good | Good |
| 6 Week Cuban | 7 | 4 | 6 | 3 |
| 6 Week Viscosity | 26.4 | 17.2 | 27.4 | 18.4 |
| 9 Week | Good | Good | Good | Good |
| 9 Week Cuban | 7 | 4 | 6 | 3 |
| 9 Week Viscosity | 26.3 | 17.7 | 25.5 | 17.4 |
| 12 Week | Good | Good | Good | Good |
| 12 Week Cuban | 5 | 4 | 6 | 3 |
| 12 Week Viscosity | 21.2 | 17.3 | 25.8 | 16 |
| 40° C. Stability | | | | |
| 3 Week | Good | Good | Good | OK |
| 3 Week Cuban | 9 | 6 | 9 | 4 |
| 3 Week Viscosity | 33.6 | 27.7 | 33.7 | 20.2 |
| 6 Week | Good | Good | Good | OK |
| 6 Week Cuban | 9 | 6 | 9 | 4 |
| 6 Week Viscosity | 33.4 | 25.5 | 34.5 | 21.5 |
| 9 Week | Good | Good | Good | OK |
| 9 Week Cuban | 9 | 7 | 9 | 3 |
| 9 Week Viscosity | 32.9 | 25.7 | 33.8 | 20.2 |
| 12 Week | Good | Good | Good | Thin |
| 12 Week Cuban | 8 | 7 | 9 | 3 |
| 12 Week Viscosity | 28.8 | 25.3 | 32.1 | 18.8 |

The following relates to toothpastes outside the scope of the present invention having unacceptable Cuban values, viscosities and/or flavor separation.

CHALK (10-17) TOOTH PASTE
(INITIAL PROPERTIES, RT AND 40° C. STORAGE TEMPERATURE STABILITY)

| | Examples | |
|---|---|---|
| Carrageenan Process | Toothpaste A HOT | Toothpaste B HOT |
| Alcohol wash Substitution | w/o IPA Wash | |
| Cuban (1 Day) | 3 | 6 |
| Toothpaste Visc (1 Day) | 14.8 | 28.7 |
| RT Stability | | |
| 3 Week | Thin | Good |
| 3 Week Cuban | 3 | 6 |
| 3 Week Viscosity | 13.6 | 28.9 |
| 6 Week | Thin | Good |
| 6 Week Cuban | 3 | 6 |
| 6 Week Viscosity | 13.1 | 28.8 |
| 9 Week | Thin | Good |
| 9 Week Cuban | 3 | 6 |
| 9 Week Viscosity | 13.1 | 28.2 |
| 12 Week | Thin | Good |
| 12 Week Cuban | 3 | 6 |
| 12 Week Viscosity | 13 | 28.9 |
| 40° C. Stability | | |
| 3 Week | Thin | Thick |
| 3 Week Cuban | 3 | 12 |
| 3 Week Viscosity | 14.8 | 46.7 |
| 6 Week | Thin | Thick |
| 6 Week Cuban | 3 | 12 |
| 6 Week Viscosity | 14.5 | 45.5 |
| 9 Week | Thin | Thick |
| 9 Week Cuban | 3 | 12 |
| 9 Week Viscosity | 14.6 | 44.1 |
| 12 Week | Severe Flavor Separation | Thick |
| 12 Week Cuban | — | 12 |
| 12 Week Viscosity | — | 44.6 |

Acceptable viscosity ranges, as measured in torque %, for the toothpastes tests were considered to be from 15 torque % to torque 40%. When the viscosity was less than 15 torque %, the toothpaste was observed to be too thin raising manufacturing issues and use issues. When the viscosity was higher than 40 torque %, the toothpaste was observed to be too thick raising other manufacturing issues such as difficulty in extruding the toothpaste.

The foregoing testing shows the acceptable Cuban values and viscosity for the toothpastes of the present invention over the entire time and temperature range that was tested. In comparison, Comparative Toothpaste A showed severe flavor separation and unacceptably low viscosities throughout its testing, while Comparative Toothpaste B showed unacceptable viscosities and Cuban values at elevated temperatures throughout its test period.

While the invention has been described in detail and with reference to specific embodiments thereof, it will be apparent to one skilled in the art that various changes and modifications can be made therein without departing from the spirit and scope thereof

What is claimed is:

1. A toothpaste composition comprising a binder, an abrasive, a humectant, a foaming agent, and water, said binder comprising a carrageenan product comprising a semi-refined, alkali treated iota carrageenan, wherein said semi-refined, alkali treated iota carrageenan has: (i) a viscosity of 18 cP to 83 cP, (ii) a particle size of at least 90% passing through a #100 US sieve mesh and at least 20% passing through a #230 US sieve mesh, and (iii) a sodium cation content of at least 35%, wherein said sodium cation content is determined by the weight of sodium cations divided by the sum of the weight of sodium cations and potassium cations in said semi-refined, alkali treated iota carrageenan; and wherein said toothpaste composition tested on twelve week stability tests at 40° C. has Cuban values of from 3-9 and viscosity of from 15-40 torque %.

2. The toothpaste composition of claim 1, wherein the binder further comprises refined carrageenan.

3. The toothpaste composition of claim 1, wherein the binder is present in an amount of from 0.3 wt % to 2.0 wt % of the composition.

4. The toothpaste composition of claim 1, wherein said carrageenan product comprises up to 10% of the total binder.

5. The toothpaste composition of claim 1, wherein said carrageenan product comprises up to 20% of the total binder.

6. The toothpaste composition of claim 1, wherein said carrageenan product comprises between 20% and 50% of the binder.

7. The toothpaste composition of claim 1, wherein said carrageenan product comprises more than 31% of the binder.

8. The toothpaste composition of claim 1, wherein said carrageenan product comprises 35% to 75% of the binder.

9. The toothpaste composition of claim 1, wherein said carrageenan product comprises more than 50% of the binder.

10. The toothpaste composition of claim 1, wherein said carrageenan product comprises 50% to 100% of the binder.

11. The toothpaste composition of claim 1, wherein the abrasive is selected from the group consisting of silica, chalk, dicalcium phosphate and mixtures thereof.

12. The toothpaste composition of claim 1, wherein the abrasive comprises chalk and the humectant comprises at least one of sorbitol, glycerin, or polyethylene glycol.

13. The toothpaste composition of claim 1, wherein the abrasive comprises chalk and the humectant comprises sorbitol, glycerin, and polyethylene glycol.

14. The toothpaste composition of claim 1, further comprising an active ingredient.

15. The toothpaste composition of claim 1 further comprising an ingredient selected from the group consisting of a fluoride, an anti bacterial agent, a desensitizing agent, an anti-tartar agent, sodium bicarbonate, an enzyme, a non-sugar sweetener, a herbal extract, a whitening agent, and a bioadhesive additive.

16. The toothpaste of claim 1, further comprising an ingredient selected from the group consisting of a flavoring agent, a coloring agent and a sweetening agent.

17. The toothpaste composition of claim 1, further comprising 1 to 5 wt % of polyethylene glycol.

18. The toothpaste composition of claim 17, wherein said polyethylene glycol is present in an amount of 2 wt %.

19. The toothpaste composition of claim 17, wherein said polyethylene glycol has an average molecular weight of between 150 to 650.

20. The toothpaste composition of claim 17, wherein said polyethylene glycol has an average molecular weight of between 190 to 210.

21. The toothpaste composition of claim 17, wherein said polyethylene glycol has an average molecular weight of between 285 to 315.

22. The toothpaste composition of claim 17, wherein said polyethylene glycol has an average molecular weight of between 380 to 420.

23. The toothpaste composition of claim 17, wherein said polyethylene glycol has an average molecular weight of between 570 to 630.

24. The toothpaste composition of claim 1, wherein said semi-refined, alkali treated iota carrageenan has a viscosity of 20 cP to 40 cP and a particle size of at least 60% passing through a #230 US sieve mesh and at least 60% passing through a #325 US sieve mesh.

25. The toothpaste composition of claim 24, wherein said semi-refined, alkali treated iota carrageenan has a viscosity between 20 cP and 30 cP.

26. The toothpaste composition of claim 25, wherein said semi-refined, alkali treated iota carrageenan has less than 4.5% by weight of potassium.

27. The toothpaste composition of claim 1, wherein said sodium cation content of said semi-refined, alkali treated iota carrageenan is at least 90%.

28. A toothpaste composition comprising a binder, an abrasive, a humectant, a foaming agent, and water, said binder comprising a carrageenan product comprising a semi-refined, alkali treated iota carrageenan, wherein said semi-refined, alkali treated iota carrageenan has: (i) a viscosity of 18 cP to 83 cP, (ii) a particle size of at least 90% passing through a #100 US sieve mesh and at least 20% passing through a #230 US sieve mesh, and (iii) a sodium cation content of at least 35%, wherein said sodium cation content is determined by the weight of sodium cations divided by the sum of the weight of sodium cations and potassium cations in said semi-refined, alkali treated iota carrageenan;

and wherein:
(1) said toothpaste composition tested on twelve week stability tests at 40° C. has Cuban values of from 3-9 and viscosity of from 15-40 torque %;
(2) the binder is present in an amount of from 0.3 wt % to 2.0 wt % of the composition; and
(3) said carrageenan product comprises up to 20% of the total binder.

29. The toothpaste composition of claim 28 wherein said carrageenan product comprises up to 10% of the total binder.

* * * * *